United States Patent [19]

Kobold et al.

[11] Patent Number: 5,631,140
[45] Date of Patent: May 20, 1997

[54] METHOD FOR THE QUANTITATIVE DETERMINATION OF GLYCATED PROTEINS

[75] Inventors: Uwe Kobold, Wielenbach; Doris Renauer, Graefelfing; Andreas Finke, Penzberg; Johann Karl, Peissenberg, all of Germany

[73] Assignee: Boehringer Mannheim GmbH, Mannheim, Germany

[21] Appl. No.: 503,224

[22] Filed: Jul. 17, 1995

[30] Foreign Application Priority Data

Jul. 18, 1994 [DE] Germany .................. 44 25 162.9

[51] Int. Cl.$^6$ .................................................. C12Q 1/34
[52] U.S. Cl. .................................................. 435/23; 435/24
[58] Field of Search .................................... 435/4, 23, 24, 435/240.27

[56] References Cited

U.S. PATENT DOCUMENTS

| 4,727,036 | 2/1988 | Knowles et al. | 436/547 |
| 5,370,990 | 12/1994 | Staniford et al. | 435/4 |

FOREIGN PATENT DOCUMENTS 0526150   7/1992   European Pat. Off. .

OTHER PUBLICATIONS

Landin, B., Rare Beta Chain Hemoglobin Variants Found in Swedish Patients During HBA1c Analysis, Hemoglobin, 17(4) 303–318 1993.

Schluter, M., Isolation of Glycopeptides Containing Individual glycosylation Sites of Friend Murine Leukemia Virus Glycoprotein, 138 305–314 1985. .

*Hemoglobin* vol. 17, No. 4, Apr. 1993, "Rare .beta.–Chain Hemoglobin Variants found in Swedish Patients During HbAlc Analysis".

*Carbohydr. Res.* (1985), 138(2), 305–14, "Isolation of glycopeptides containing individual glycopeptides by methylation analysis".

"Arbeitsanleitung Klinische Chemie", 1992. By Merck, Diagnostica (German).

*Primary Examiner*—Ralph Gitomer
*Attorney, Agent, or Firm*—Nikaido Marmelstein Murray & Oram LLP

[57] ABSTRACT

Method for the quantitative determination of glycated protein in particular haemoglobin and HbA1c, wherein the respective sample is firstly contacted with a proteolytic enzyme and subsequently a non-immunological chromatographic separation process is carried out.

19 Claims, 5 Drawing Sheets

METHOD FOR THE QUANTITATIVE DETERMINATION OF GLYCATED PROTEINS

BACKGROUND OF THE INVENTION

The invention concerns a method for the quantitative determination of glycated protein and especially haemoglobin (HbA1c), which is essentially composed of an enzymatic and a chromatographic method step. Subsequently the exact amount of HbA1c is determined by a differential measurement of for example glycated and non-glycated haemoglobin (HbA0). Alternatively the absolute content of glycated and non-glycated proteins can be determined by calibration with suitable standard materials.

There are numerous methods for determining glycated proteins. These can be basically divided into three groups depending on the way in which glycated and non-glycated protein components are separated and quantified (Clin. Chemistry 32 (1986), B64–B70). The first group consists of physicochemical methods based on the utilization of charge differences. These include the HPLC determination with cation exchanger columns such as Diamat, MonoS and PolyCat A (Bisse method) which are the most frequently used methods in clinical chemistry. In the case of haemoglobin for example the quantitative evaluation is carried out by a relative measurement of the HbA1c signal in relation to the total amount of Hb (% HbA1c).

Methods in the second group are those which utilize the different chemical reactivity of glycated and non-glycated protein. These include the thiobarbituric acid method in which for example the glucose bound to haemoglobin is converted into a yellow dye and measured photometrically and also affinity chromatography methods in which complex formation between the vicinal diol groups of the sugar residue and a boric acid group that is bound covalently to a support is used to separate glycated and non-glycated haemoglobin. The separated substance classes are quantified photometrically and the relative amount of glycated haemoglobin is calculated or, in the case of the thiobarbituric acid method quantified, as an absolute determination by calibration with suitable standard materials.

Thirdly, immunological methods may be mentioned. Specific antibodies are used in immunological methods. These recognize for example the structural unit at the N-terminal end of the β chain of the glycated haemoglobin molecule which is typical for HbA1c (e.g. Tina quant® HbA1c, Boehringer Mannheim). In the immunological methods the absolute content of the respective protein is determined. This necessitates the use of calibrators which have been assigned a target concentration by an independent method. The relative content of for example HbA1c cannot be obtained by a direct measurement.

The known methods are, however, associated with a number of disadvantages. Thus some of the physicochemical methods have a very poor selectivity since the measured signals of glycated protein are overlapped by the non-glycated variants. The shapes of the chromatographic peaks are often asymmetrical and difficult to integrate. The cation exchanger columns that are used are susceptible to small changes in the working conditions and to contamination. Due to the poor selectivity there is a high risk of measuring values that are too high (false positive values).

In the case of chemical methods it is difficult to standardize the procedure and interferences by other components containing sugar can only be avoided with a large amount of effort. It is not possible to differentiate between for example HbA1c and other glycated haemoglobin variants.

The immunological methods are characterized by a very high selectivity towards glycated protein variants. However, the quality of the results depends on the quality of the standard used for calibration. Suitable primary standards in an optimal quality are not at present available, in particular for HbA1c. Information on matrix dependencies cannot be obtained due to a lack of a suitable reference method. In this case false positive values are also frequently obtained (see for example J. Clin. Lab. Anal. 8, (1994), 128–134).

SUMMARY OF THE INVENTION

The object of the invention is therefore to provide a method which overcomes the disadvantages of the known methods. The object is achieved by firstly treating an aqueous sample containing a glycated protein or corresponding variants with a proteolytic enzyme and subsequently separating the resulting mixture containing the fragments by chromatography.

BRIEF DESCRIPTION OF THE DRAWING

FIG. 1 shows the result of the method according to the invention (sample: whole blood haemolysate; enzymatic treatment and chromatograph (HPLC)).

FIGS. 2 and 3 show the result of the method according to the invention (sample: preparatively purified HbA1c; 2: cation exchanger; 3: cation exchanger and affinity chromatography).

FIG. 4 shows the result of the method according to the invention (sample: preparatively purified HbA0 (cation exchanger)),

FIG. 5 shows the result of the method according to the invention (sample: whole blood haemolysate, enzymatic treatment and chromatography (HPLC)).

DESCRIPTION OF THE PREFERRED EMBODIMENTS

Figure 1:
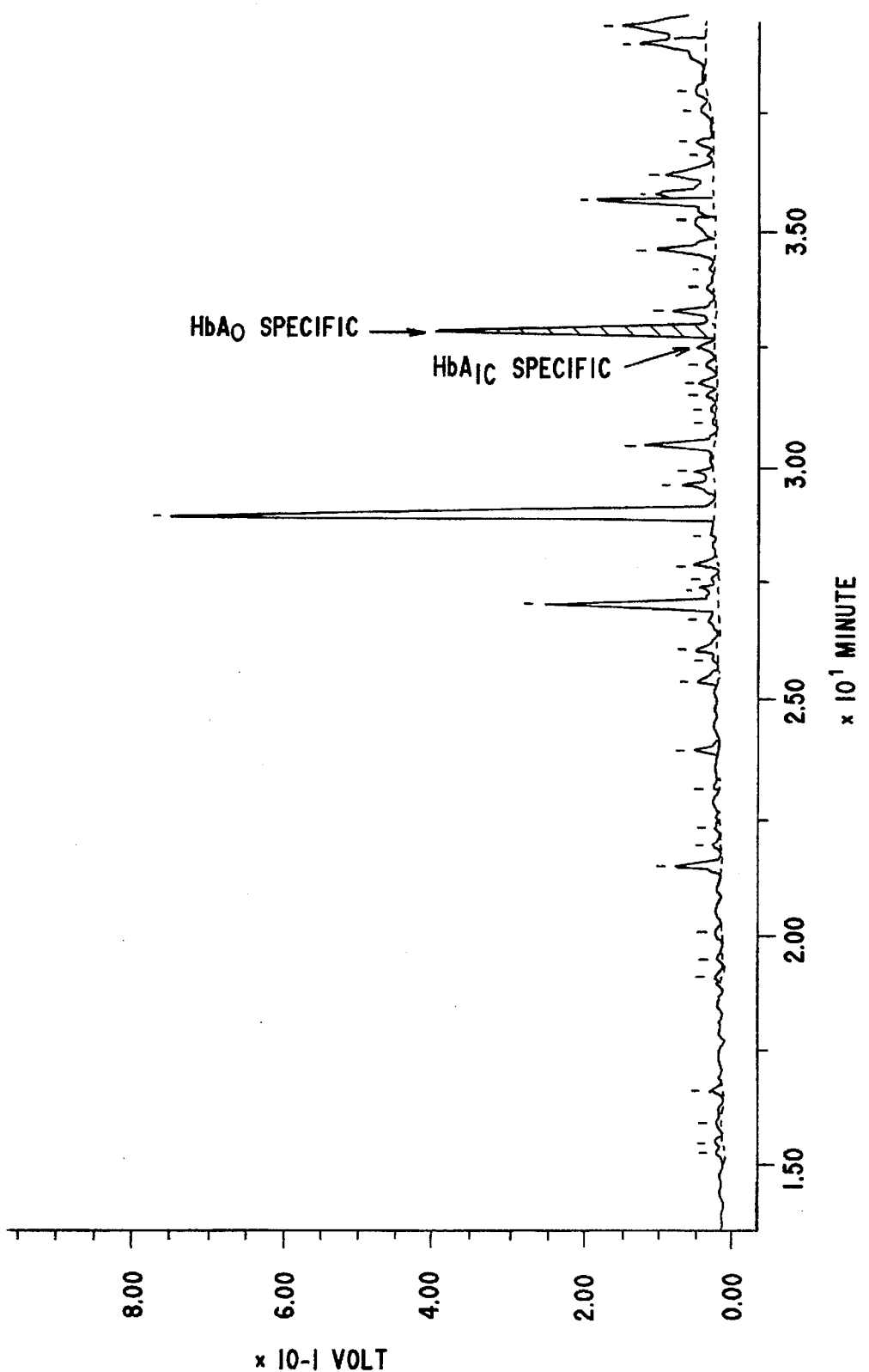
FIG. 1

The sample material, in particular haemolysed whole blood, is incubated with a proteolytic enzyme in a suitable reaction buffer. Haemolysis is carried out by known methods. Proteases which are capable of cleaving a N-terminal peptide which is as short as possible from the β chain of haemoglobin have proven to be suitable in this case as the enzyme. Apart from trypsin, chymotrypsin and thermolysin in particular and especially endoproteinase Glu-C have proven to be suitable for this. The proteolytic enzymes are usually used at a concentration of $\frac{1}{200}$ to $\frac{1}{10}$ of the amount by weight of protein.

Examples of suitable reaction buffers are ammonium carbonate and/or sodium phosphate buffer which are usually used at concentrations of up to approximately 10 mM in a pH range of 3.5–8.5 and, depending on the respective protease, may be supplemented by further auxiliary substances such as activators and/or stabilizers such as e.g. sodium dodecyl sulphate, urea, guanidine hydrochloride or acetonitrile.

The incubation with the respective proteolytic enzyme is carried out between 20° C. and 40° C., preferably at ca. 25° C. and can be completed after several minutes to a maximum of 18 hours depending on the enzyme.

In addition it has proven to be particularly advantageous when the erythrocytes are separated before haemolysis and to carry out the haemolysis merely with water.

The solution obtained by enzyme treatment contains specific peptides for the proteins to be determined in each case in addition to other fragments. The peptide mixtures are subsequently separated in a HPLC process with good resolution (e.g. reversed phase materials) and detected photometrically. Such separation methods are generally known to a person skilled in the art (e.g. K. L. Stone, J. I. Elliot, G. Peterson, W. McMurray, K. R. Williams, "Reversed-phase high performance liquid chromatography for fractionation of enzymatic digests and chemical cleavage products of proteins", Methods in Enzymology, 193 (1990), 389–412). Alternatively it is also possible to use other separation methods such as e.g. capillary electrophoresis (e.g. Capillary Electrophoresis Separations of Peptides: Practical Aspects and Applications, Chap. 9, p. 237–271 in Capillary Electrophoresis, Academic Press 1992).

The simultaneous selective determination of glycated and non-glycated protein is possible from the measured signal intensities of the glycated and the respective amount of non-glycated peptide. In the analytical evaluation the percentage of glycated protein in relation to non-glycated protein is obtained. The method is particularly advantageous for the determination of HbA1c in addition to non-glycated haemoglobin (HbA0). This method has proven to be highly specific and free from any type of interference, moreover the determination of the percentage content of HbA1c is possible without additional calibration or standardization.

The invention is elucidated further by the following examples.

EXAMPLE 1

The method was carried out using a whole blood haemolysate and HbA1c and HbA0 standard materials purified in different ways. In each case the N-terminal peptide with a length of twenty-two amino acids was used to quantify HbA1c and HbA0.

For purposes of comparison, the samples used were also measured with a HPLC method based on a cation exchanger (PolyCat A, Bisse method) without prior enzyme treatment.

A According to the invention (enzyme+HPLC)

A.1 Enzyme solution:
Endoproteinase Glu-C (sequencing grade Boehringer Mannheim; Cat. No. 1047817)
Protein concentration: ca. 1 mg/ml
Ratio protein: enzyme 20:1
25 mM ammonium acetate buffer containing 5% acetonitrile
pH 4.0
Enzymatic treatment, conditions: 18 h, 25° C.

A.2 HPLC step, conditions:
HPLC system HP 1090
Separation column Zorbax C8 stable bond
Gradient elution from water to acetonitrile containing 0.1% trifluoroacetic acid (TFA)
Detection at 214 nm B. HPLC step without prior enzymatic treatment
Column material: polyCatA
Procedure according to E. Bisse & H. Wieland, J. of Chromat. 434 (1988) 95–110

The results show that the selectivity of the cation exchanger chromatography alone does not meet the requirements; a false positive deviation of ca. 15% is found. The results of both methods are comparable in the case of sample material which was purified by affinity chromatography and no longer contains non-glycated haemoglobin since now the HbA1c signal in the cation exchanger chromatography can no longer be overlapped by non-glycated material.

TABLE 1

| Sample | % HbA1c Glu-C + HPLC | % HbA1c PolyCat A | % deviation |
| --- | --- | --- | --- |
| whole blood haemolysate | 5.5 | 6.5 | 15.4 |
| HbA1c purified preparatively cation exchanger | 7.5 | 89 | 15.7 |
| HbA1c purified preparatively affinity chromatography | 93 | 92 | –1.1 |
| HbA0 purified preparatively cation exchanger | 0 | 0.6 | |

Table 1 shows a comparison between the method according to the invention and a pure HPLC method.

EXAMPLE 2

Figure 5:
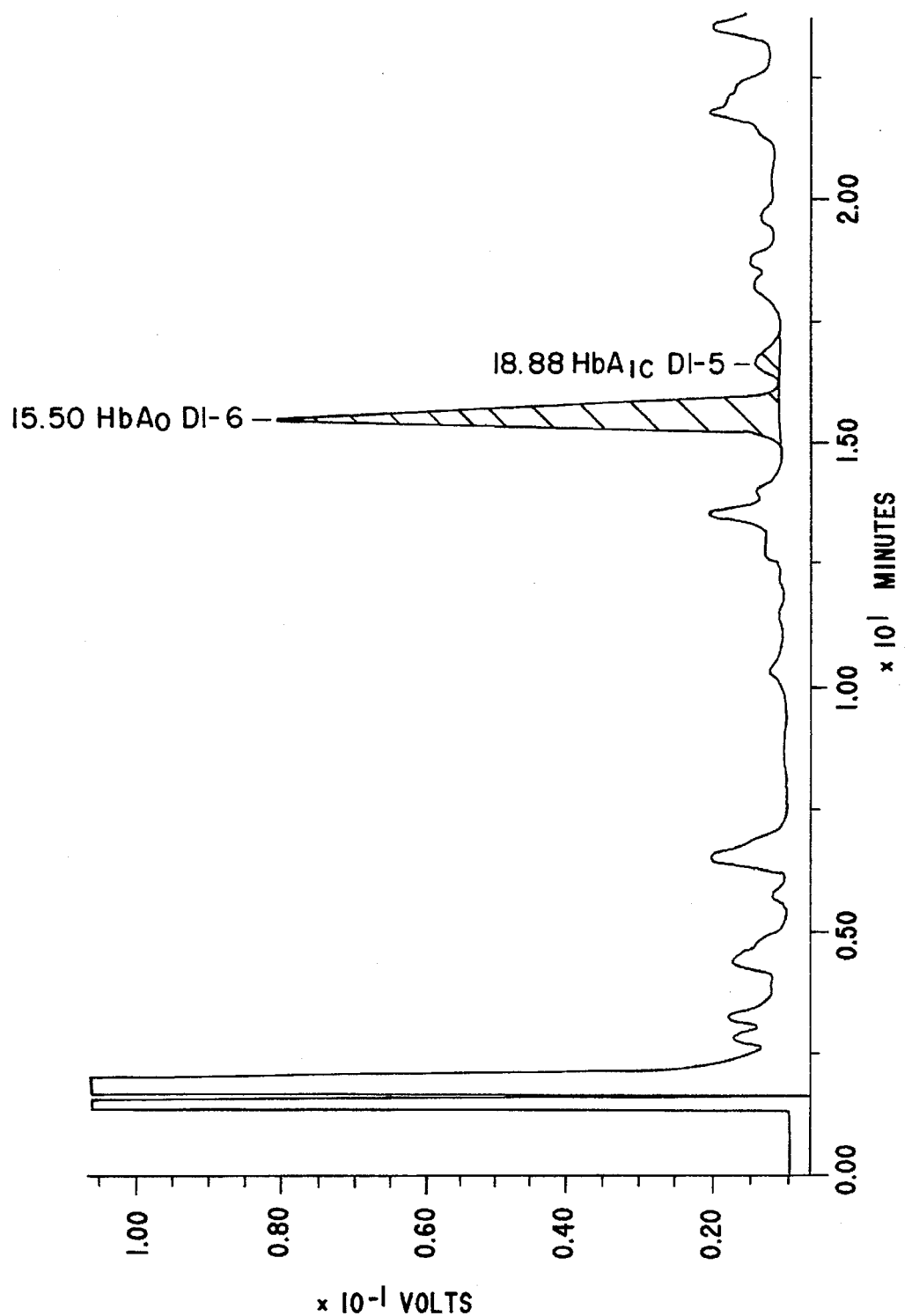
FIG. 5

In order to check the reproducibility of the method, a whole blood sample was processed several times and, after the enzymatic treatment, the N-terminal peptide with a length of 6 amino acids is used to quantify HbA1c and HbA0 (cf. chromatogram FIG. 5).

Enzyme solution:
Endoproteinase Glu-C (sequencing grade Boehringer Mannheim; Cat. No. 1047817)
Protein concentration: ca. 1 mg/ml
Ratio protein: enzyme 30:1 to 60:1
25 mM ammonium acetate buffer
pH 4.0
The results (Table 2) show that the method can be carried out very reproducibly.

TABLE 2

| Sample | Ratio Protein: Enzyme | % HbA1c (Glu-C + HPLC) |
| --- | --- | --- |
| Whole blood haemolysate prep. 1 | 43:1 | 5.35 |
| Whole blood haemolysate prep. 2 | 43:1 | 5.38 |
| Whole blood haemolysate prep. 3 | 43:1 | 5.48 |
| Whole blood haemolysate prep. 4 | 43:1 | 5.25 |
| Whole blood haemolysate prep. 5 | 43:1 | 5.44 |
| Whole blood haemolysate prep. 6 | 34:1 | 5.39 |
| Whole blood haemolysate prep. 7 | 51:1 | 5.50 |

Table 2 shows the results of a reproducibility experiment using the HPLC step according to the invention; conditions: HPLC system HP 1090
Separation column Zorbax SN-CN
Gradient elution from water to acetonitrile containing 0.1% trifluoroacetic acid
Detection at 214 nm.

FIG. 1

FIG. 1 shows the result of the method according to the invention (sample: whole blood haemolysate; enzymatic treatment and chromatography (HPLC)).

Figure 2:
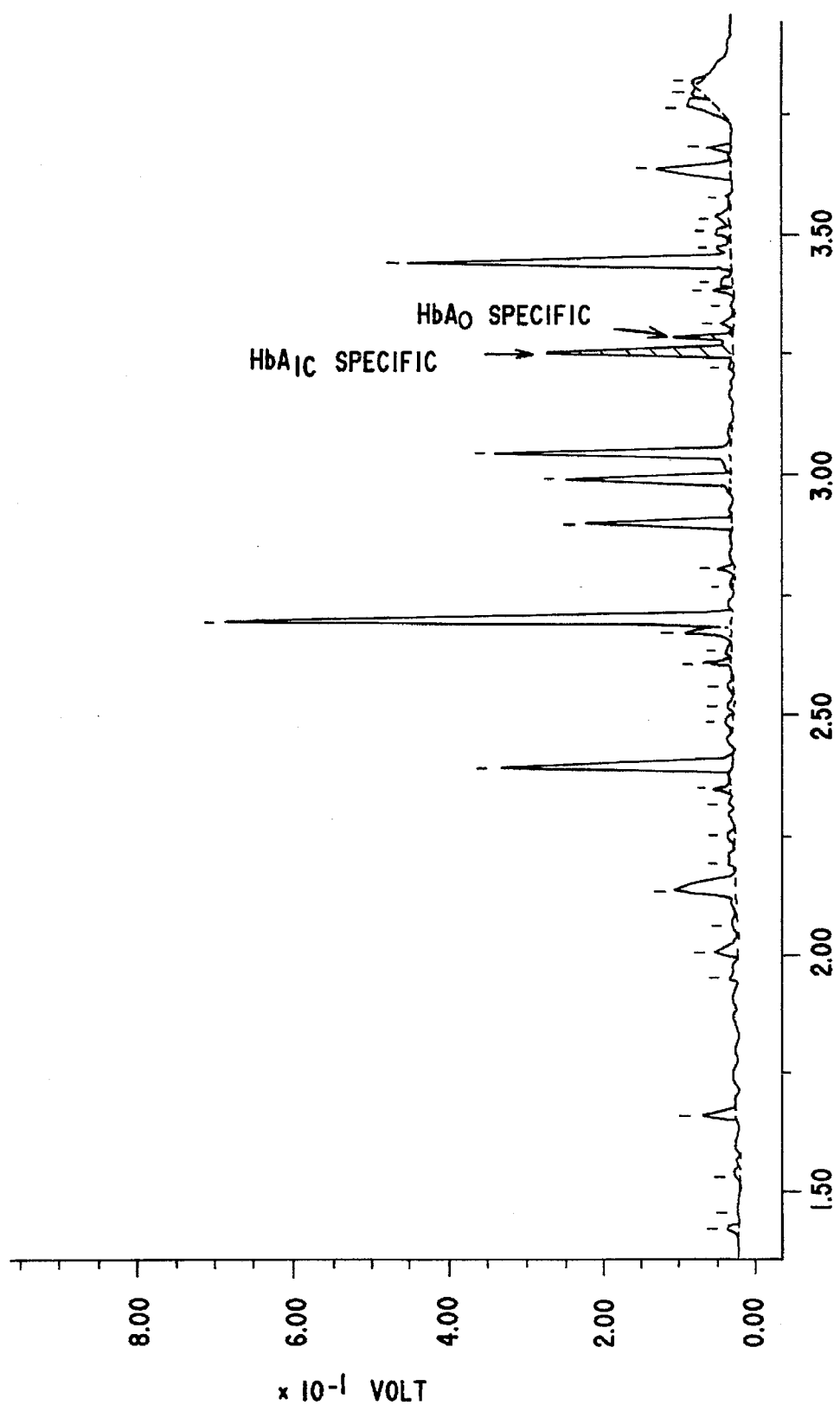
FIGS. 2 and 3
Figure 3:
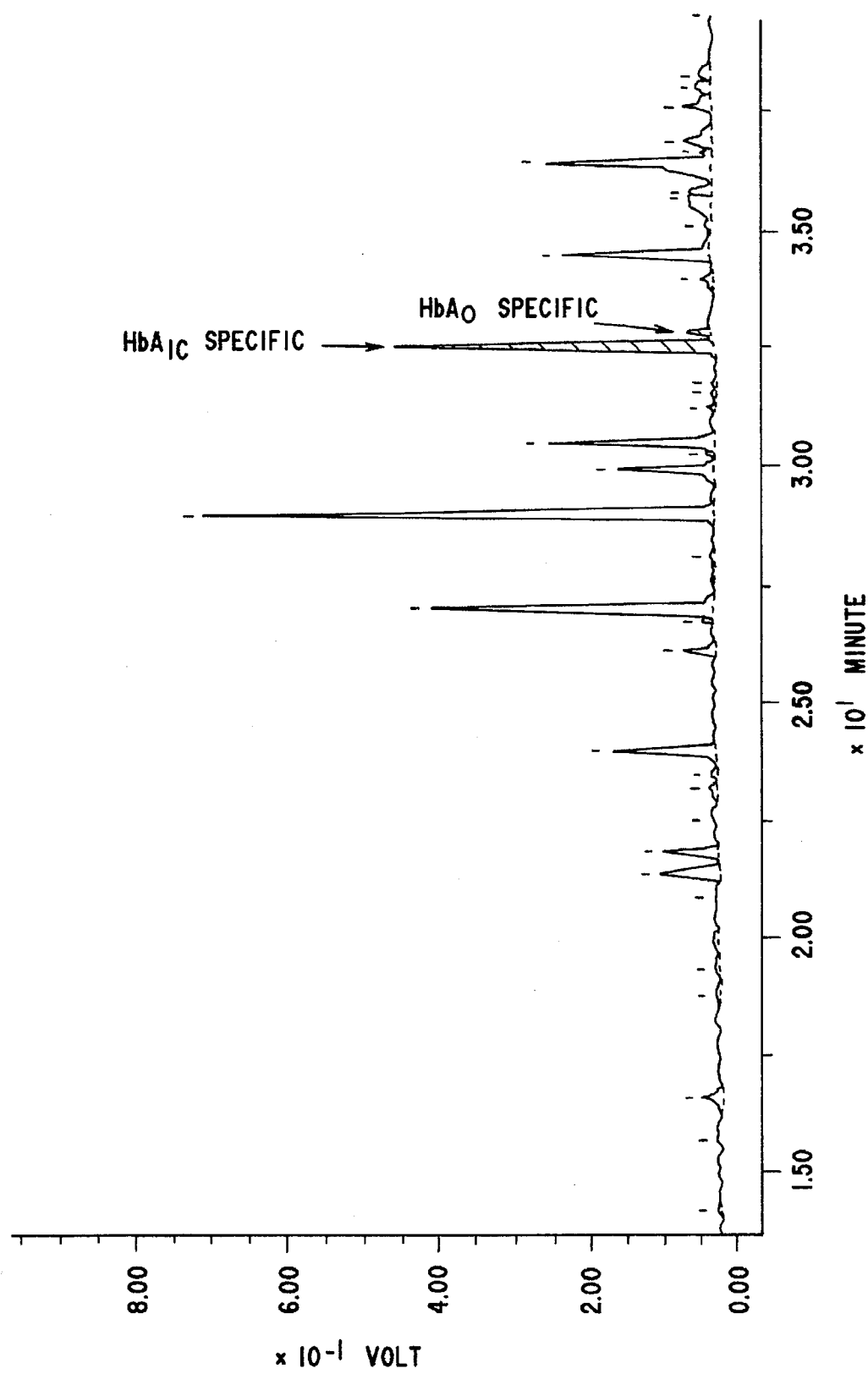

FIGS. 2 and 3

FIGS. 2 and 3 show the result of the method according to the invention (sample: preparatively purified HbA1c; 2: cation exchanger; 3: cation exchanger and affinity chromatography).

FIG. 4

Figure 4:
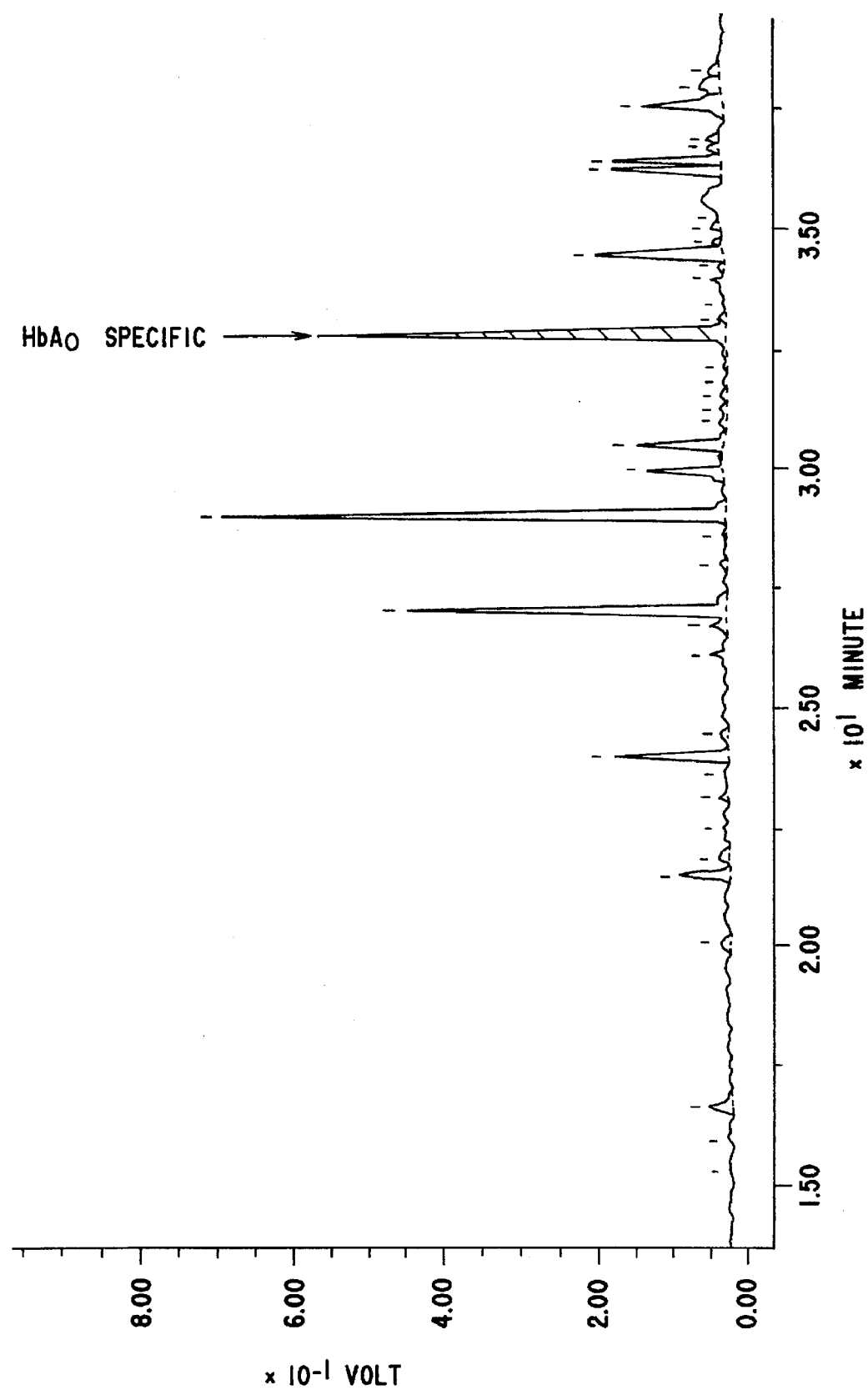
FIG. 4

FIG. 4 shows the result of the method according to the invention (sample: preparatively purified HbA0 (cation exchanger)).

FIG. 5

FIG. 5 shows the result of the method according to the invention (sample: whole blood haemolysate, enzymatic treatment and chromatography (HPLC)).

We claim:

1. A method for the determination of a glycated protein relative to non-glycated protein in an aqueous sample, comprising:

reacting the sample with a proteolytic enzyme to form a peptide mixture comprising an amount of glycated peptides and an amount of non-glycated peptides, separating said glycated peptides and said non-glycated peptides in said peptide mixture, and determining said glycated protein relative to said non-glycated protein by measuring the amount of said glycated peptides and the amount of said non-glycated peptides and comparing the amount of said glycated peptides with the amount of said non-glycated peptides.

2. The method according to claim 1, wherein said glycated protein is determined relative to said non-glycated protein mathematically by calculating a quotient by dividing the amount of said glycated protein by the amount of said non-glycated protein.

3. The method according to claim 1, wherein said peptide mixture is separated using a nonimmunological separation method.

4. The method according to claim 3, wherein said nonimmunological method is chromatography.

5. The method according to claim 1, wherein said sample is hemolyzed whole blood.

6. The method according to claim 1, wherein said sample is a product of a lysis of erythrocytes which erythrocytes have been separated from whole blood.

7. The method according to claim 6, wherein said lysis is carried out with water.

8. The method according to claim 1, wherein said proteolytic enzyme cleaves an N-terminal peptide from a β-chain of hemoglobin.

9. The method according to claim 1, wherein said proteolytic enzyme is selected from the group consisting of trypsin, chymotrypsin, thermolysin and endoproteinase Glu-C.

10. The method according to claim 1, wherein said proteolytic enzyme is present at a concentration of $1/200$–$1/10$ of the amount by weight of the protein.

11. The method according to claim 3, wherein said nonimmunological separation method is HPLC chromatography or capillary-electrophoretic separation.

12. The method according to claim 11, wherein said HPLC chromatography is reverse phase HPLC.

13. The method according to claim 1, wherein said glycated protein is HbA1c.

14. The method according to claim 1, wherein said non-glycated protein is HbA0.

15. The method according to claim 1, wherein said sample is reacted with said proteolytic enzyme in a reaction buffer selected from the group consisting of an ammonium carbonate buffer, an ammonium acetate buffer, a sodium phosphate buffer and an ammonium carbonate/sodium phosphate buffer.

16. The method according to claim 15, wherein said reaction buffer has a pH between 3.5–8.5.

17. The method according to claim 15, wherein said reaction buffer further comprises at least one activator, stabilizer or activator and stabilizer.

18. The method according to claim 1, wherein said sample is reacted with said proteolytic enzyme at a temperature between 20°–40° C.

19. The method according to claim 18, wherein said sample is reacted with said proteolytic enzyme at 25° C.

* * * * *